US012642782B2

(12) United States Patent
Cavaleri

(10) Patent No.: US 12,642,782 B2
(45) Date of Patent: Jun. 2, 2026

(54) KETOGENIC COMPOSITIONS AND METHODS OF USE THEREOF

(71) Applicant: Franco Cavaleri, Surrey (CA)

(72) Inventor: Franco Cavaleri, Surrey (CA)

( * ) Notice: Subject to any disclaimer, the term of this patent is extended or adjusted under 35 U.S.C. 154(b) by 255 days.

(21) Appl. No.: 18/372,724

(22) Filed: Sep. 26, 2023

(65) Prior Publication Data

US 2024/0156771 A1 May 16, 2024

Related U.S. Application Data

(60) Provisional application No. 63/420,723, filed on Oct. 31, 2022.

(51) Int. Cl.

| | |
|---|---|
| ***A61K 31/216*** | (2006.01) |
| ***A61K 9/00*** | (2006.01) |
| ***A61K 9/48*** | (2006.01) |
| ***A61K 31/135*** | (2006.01) |
| ***A61K 31/198*** | (2006.01) |
| ***A61K 36/28*** | (2006.01) |
| ***A61K 36/77*** | (2006.01) |
| ***A61K 36/82*** | (2006.01) |
| ***A61K 36/84*** | (2006.01) |
| ***A61P 3/04*** | (2006.01) |

(52) U.S. Cl.

CPC .......... *A61K 31/216* (2013.01); *A61K 9/0053* (2013.01); *A61K 9/48* (2013.01); *A61K 31/135* (2013.01); *A61K 31/198* (2013.01); *A61K 36/28* (2013.01); *A61K 36/77* (2013.01); *A61K 36/82* (2013.01); *A61K 36/84* (2013.01); *A61P 3/04* (2018.01)

(58) Field of Classification Search

CPC ...... A61K 31/216; A61K 9/0053; A61K 9/48; A61K 31/135; A61K 31/198; A61K 36/28; A61K 36/77; A61K 36/82; A61K 36/84; A61K 9/4858; A61K 31/19; A61K 31/192; A61P 3/04

See application file for complete search history.

(56) References Cited

U.S. PATENT DOCUMENTS

2017/0042842 A1* 2/2017 Edge .................... A61K 9/0046
2017/0290792 A1* 10/2017 Cavaleri ................ A61K 36/82

FOREIGN PATENT DOCUMENTS

WO WO-2018020512 A1 * 2/2018 .............. A61P 43/00
WO WO-2020086820 A1 * 4/2020 ............. A61Q 19/06

OTHER PUBLICATIONS

Bachmann et al., "Traditional Foods as Alternatives to Synthetic Compounds" Agroscope Sep. 18, 2020 pp. 1-4. (Year: 2020).*

Devappa et al., "Forest biorefinery: Potential of poplar phytochemicals as value-added co-products" Biotechnology Advances 33 (2015) 681-716. (Year: 2015).*

Gurley et al., "Multi-ingredient, caffeine-containing Dietary Supplements: History, Safety, and Efficacy" Clinical Therapeutics/vol. 37, No. 2, 2015, pp. 275-301. (Year: 2015).*

Head et al., "Nutrients and Botanicals for Treatment of Stress: Adrenal Fatigue, Neurotransmitter Imbalance, Anxiety, and Restless Sleep" Alternative Medicine Review, vol. 14, No. 2, 2009, pp. 114-140. (Year: 2009).*

Wang et al., "Chlorogenic acid alleviates obesity and modulates gut microbiota in high-fat-fed mice" Food Sci Nutr. 2019; 7: 579-588. (Year: 2019).*

* cited by examiner

*Primary Examiner* — Aradhana Sasan

(57) ABSTRACT

Compositions and methods for providing a person with an exogenous and therapeutically effective supply of short chain fatty acids, chlorogenic acid, and, optionally, ketones are disclosed. The compositions include one or more short chain fatty acids (such as butyric acid, butyrate salts, propionic acid, propionate salts, acetic acid, or acetate salts); chlorogenic acid; and, optionally, one or more beta-hydroxybutyrate salts. The compositions and methods are useful for inducing ketosis and/or beta-oxidative activity in a subject. In addition, compositions that include concentrated forms of, and methods of using, chlorogenic acid (alone or in combination with short chain fatty acids and ketones) to induce ketogenesis in a subject are disclosed.

2 Claims, 2 Drawing Sheets

CONTROL
PRE-TREATED FAT CELLS

24 HOURS POST-TREATMENT

ISOLATED FAT CELLS

ISOLATED FAT CELLS

| | Subject Weight (Pounds) | | | | | | | |
|---|---|---|---|---|---|---|---|---|
| Subjects | Week 1 | Week 2 | Week 3 | Week 4 | Week 5 | Week 6 | Week 7 | Total Weight Loss |
| TC | 199 | 194 | 188 | 184 | 183 | 183 | 182 | 17 |
| MC | 125 | 122 | 121 | 119 | 116 | 116 | 114 | 11 |
| CW | 148 | 144 | 142 | 138 | 132 | 130 | 131 | 17 |
| FC | 195 | 194 | 190 | 186 | 183 | 183 | 181 | 14 |
| NC | 187 | 187 | 183 | 179 | 173 | 171 | 170 | 17 |
| MS | 189 | 188 | 184 | 180 | 175 | 174 | 170 | 19 |

FIGURE 2

KETOGENIC COMPOSITIONS AND METHODS OF USE THEREOF

CROSS-REFERENCE TO RELATED APPLICATIONS

This application claims priority to, and incorporates by reference, U.S. provisional patent application Ser. No. 63/420,723, filed on Oct. 31, 2022.

FIELD OF THE INVENTION

The field of the present invention relates to certain compositions (and methods of use thereof) that comprise a combination of short chain fatty acids (such as butyrate salts); chlorogenic acid; and, optionally, ketones (such as beta-hydroxybutyrate salts), which provide the various health benefits described herein. In addition, the field of the present invention relates to certain methods of using chlorogenic acid (alone or in combination with short chain fatty acids and, optionally, ketones) to induce ketogenesis, beta-oxidative activity, and weight loss in a subject.

BACKGROUND OF THE INVENTION

It is well understood that dietary restriction in the form of calorie deprivation and/or a low carbohydrate/high fat diet is conducive to ketogenesis. Although hyperketonemia (>0.5 mmol/L of serum ketones), when induced by such dietary programs, has been shown to produce positive effects on biological markers of insulin resistance, serum glucose stabilization, diabetes, obesity, epilepsy, cognitive deficits, inflammation and even cancer, achievement and sustenance of functional serum ketone levels is a very difficult task. Sustained ketosis is also a state desired by athletes in pursuit of improved performance, as a function of ketones serving as substrates for mitochondrial ATP generation. However, achieving a state of ketosis requires dedication and sacrifice, while enduring states of malaise during energy substrate transition. For some, the achievement of ketosis is more difficult than for others based on metabolic, genetic, environmental, and lifestyle factors combined.

In view of the foregoing, there is a continuing need for compositions and methods for inducing ketosis and beta-oxidative activity in a person. Such compositions will preferably provide an exogenous supply of short chain fatty acids, chlorogenic acid, and other agents that are effective to induce ketosis and beta-oxidative activity in a person (and to provide a person with the numerous pharmacologic benefits described herein). In other embodiments, the compositions and methods may entail the delivery of certain concentrated forms of only chlorogenic acid.

SUMMARY OF THE INVENTION

According to certain aspects of the invention, compositions are provided that include combinations of chlorogenic acid; one or more sources of short chain fatty acids (e.g., butyric acid, butyrate salts, propionic acid, propionate salts, acetic acid, or acetate salts); and, optionally, one or more sources of ketones (e.g., one or more beta-hydroxybutyrate salts). In other aspects of the invention, certain concentrated forms of chlorogenic acid are provided, which are effective for inducing ketogenesis in a subject. Such concentrated forms of chlorogenic acid may be used alone or, optionally, in combination with short chain fatty acids and, optionally, one or more sources of ketones (e.g., one or more beta-hydroxybutyrate salts).

The compositions of the present invention offer a multitude of benefits and can be used for numerous applications. For example, in some embodiments, oral formulations of such compositions may be used for sustaining elevated lumen and serum short chain fatty acid and/or ketone concentrations intended for therapeutic applications, such as body mass alteration, support of insulin activity, and support of cognitive activity (despite probiotic (microbiome) status and diet). More particularly, the compositions of the invention may be useful for inducing ketosis in a subject; inducing beta-oxidative activity in a subject; and/or treating or preventing obesity, insulin resistance, metabolic syndromes, cognitive deficits, IBS, IBD, epilepsy, atrophy, and catabolism.

The above-mentioned and additional features of the present invention are further illustrated in the Detailed Description contained herein.

BRIEF DESCRIPTION OF THE FIGURES

FIG. 2: a table summarizing the results of a human weight loss study involving a composition of the present invention.

DETAILED DESCRIPTION OF THE INVENTION

Figure 1:
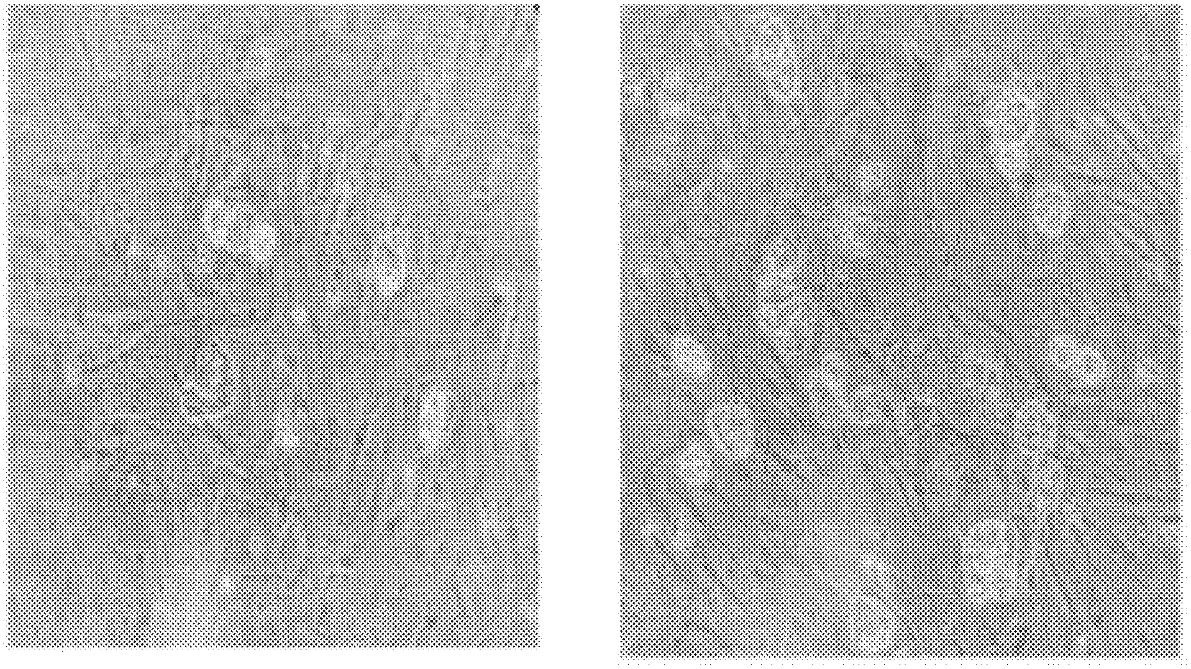
FIG. 1: two histology slides showing the effects of a composition of the present invention on brown fat cell differentiation and activation.

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments of the present invention, the compositions may comprise or, in other embodiments, consist essentially of (a) chlorogenic acid; (b) one or more sources of short chain fatty acids (such as butyric acid, butyrate salts, propionic acid, propionate salts, acetic acid, or acetate salts); and, optionally, (c) purified beta-hydroxybutyrate or esters or propionate salts thereof (such as one or more beta-hydroxybutyrate salts). The invention provides that the compositions may optionally further include other pharmacologically active agents, such as potassium citrate, magnesium citrate, green tea extract, guarana extract, L-theanine, phenethylamine, L-tryptophan, valerian root extract, chamomile flower extract, passion fruit extract, ferulic acid, octacosanol, and/or one or more vitamins (such as Vitamin D).

Still further, the invention provides that the compositions of the present invention encompass chlorogenic acid and one or more sources of short chain fatty acids (such as butyric acid or butyrate salts) as separate, but mixed, chemical components; whereas, in other embodiments, the chlorogenic acid and one or more sources of short chain fatty acids (such as butyric acid or butyrate salts) may be covalently bonded to each other. In addition, the invention provides that the chlorogenic acid may exist in a natural extract, such as green tea extract, or the chlorogenic acid may exist in a purified form, such as at least 75%, 80%, 85%, 90%, or 95% purified (i.e., free from other compositions). The invention provides that the one or more sources of short chain fatty acids (such as butyric acid, butyrate salts, propionic acid, propionate salts, acetic acid, or acetate salts) will exist in a purified form, such as at least 75%, 80%, 85%, 90%, or 95% purified (i.e., free from other compositions).

In other embodiments of the invention, certain concentrated forms of chlorogenic acid are provided, which are effective for inducing ketogenesis in a subject. The invention provides that such concentrated forms of chlorogenic acid will preferably deliver 100-2,000 mg of chlorogenic acid to a subject, on a per serving basis. Such concentrated forms of chlorogenic acid may be used alone or, optionally, in combination with short chain fatty acids (e.g., butyric acid or butyrate salts) and/or, optionally, in combination with one or more sources of ketones (e.g., one or more beta-hydroxybutyrate salts).

As used herein, unless otherwise stated, chlorogenic acid refers to the ester of caffeic acid and (−)-quinic acid, along with all related polyphenol esters and derivatives thereof. The IUPAC name for chlorogenic acid is (1S,3R,4R,5R)-3-{[(2E)-3-(3,4-Dihydroxyphenyl)prop-2-enol]oxy}-1,4,5-trihydroxycyclohexane-1-carboxylic acid, which is known to have the chemical structure shown below:

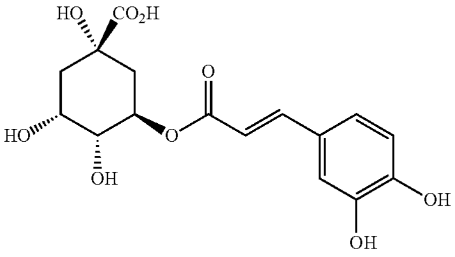 [SMILES: O=C(/C=C/c1ccc(O)c(O)c1)O[C@@H]1C[C@](O)(C(=O)O)C[C@@H](O)[C@H]1O]

The invention provides that the short chain fatty acids that are included in the compositions may be derived from, for example, acetic acid, propionic acid, butyric acid, isobutyric acid, valeric acid, and/or isovaleric acid. In certain preferred embodiments, the compositions will include butyric acid (IUPAC name is butanoic acid) as the primary source of short chain fatty acids, which has the chemical structure shown below:

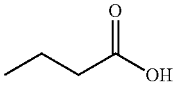

In certain preferred embodiments, the invention provides that butyric acid is included in the form of one or more butyrate salts, such as butyrate sodium salt, butyrate calcium salt, and/or butyrate magnesium salt.

The invention provides that the one or more optional sources of ketones included in the compositions are preferably derived from one or more beta-hydroxybutyrate salts, such as beta-hydroxybutyrate sodium salt; beta-hydroxybutyrate calcium salt; beta-hydroxybutyrate magnesium salt; and/or beta-hydroxybutyrate phosphorus salt. Such beta-hydroxybutyrate salts have the general chemical structure shown below, in which "X" is a metal ion (such as a sodium, calcium, magnesium, or phosphorus ion).

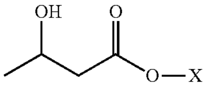

The invention provides that, in certain embodiments of the present invention, the compositions may further include citrates, such as potassium citrate and/or magnesium citrate. The invention provides that such citrates will provide a subject with additional and preferred amounts of electrolytes and metabolic enhancements. In addition, the compositions may optionally include green tea extract and/or guarana extract to provide a natural source of caffeine to support beta oxidation of fatty acids and ketosis induction. Such green tea extract and/or guarana extract will supply a significant amount of high-epigallocatechin gallate (EGCG) for optimal antioxidant support, and it will provide anti-amylase activity to inhibit or slow carbohydrate digestion to result in an impaired glycemic index of and serum contribution by dietary carbohydrate sources, which promotes a ketogenic environment.

According to certain preferred embodiments of the present invention, the compositions are formulated to deliver (in a single dose) 50 mg-1500 mg of chlorogenic acid and 50 mg-1,000 mg of short chain fatty acids (e.g., butyrate salts) or, more preferably, 100 mg-500 mg of chlorogenic acid and 50 mg-250 mg of short chain fatty acids (e.g., butyrate salts); and, optionally, 50-10,000 mg of ketones (e.g., one or more beta-hydroxybutyrate salts). More particularly, the methods and compositions (e.g., a single dose) are preferably effective to deliver (A) at least 50 mg, 100 mg, 150 mg, 200 mg, 300 mg, 400 mg, or 500 mg of chlorogenic acid; (B) at least 50 mg, 100 mg, 150 mg, 200 mg, 250 mg, 300 mg, 400 mg, 500 mg, or 600 mg of short chain fatty acid (e.g., butyric acid, butyrate salts, propionic acid, propionate salts, acetic acid, or acetate salts); and, optionally, (C) at least 50 mg, 100 mg, 200 mg, 300 mg, 400 mg, 500 mg, 600 mg, 700 mg, 800 mg, 900 mg, 1,000-2,000 mg, or 2,000-10,000 of ketone (e.g., one or more beta-hydroxybutyrate salts). As described further below (and in the Examples), such compositions may be delivered to a person in the form of oral capsules, dry powders, liquid dosages, or other suitable delivery forms.

Notwithstanding the preferred embodiments and Examples described herein, the invention provides that the compositions of the present invention may be administered in any desired and effective manner, e.g., as pharmaceutical compositions or nutritional supplements for oral ingestion. More particularly, for example, pharmaceutically acceptable compositions or nutritional supplements of the invention may comprise one or more of the compositions described herein with one or more acceptable carriers. Regardless of the route of administration selected, the compositions may be formulated into acceptable dosage forms by conventional methods known to those of skill in the art. For example, acceptable carriers include, but are not limited to, sugars (e.g., lactose, sucrose, mannitol, and sorbitol), silicon dioxide, starches, cellulose preparations (such as microcrystalline cellulose), calcium phosphates (e.g., dicalcium phosphate, tricalcium phosphate and calcium hydrogen phosphate), sodium citrate, water, aqueous solutions, alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes, paraffins, silicones, talc, silicylate, etc.

Each acceptable carrier used in a pharmaceutical composition or nutritional supplement of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions and nutritional supplements of the invention may, optionally, contain additional ingredients and/or materials commonly used in pharmaceutical compositions and/or nutritional supplements. These ingredients and materials include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxy methyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; (28) vitamins and minerals; (29) proteins that carry therapeutic or nutritional benefits, such as whey protein and other milk-derived proteins; and (30) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions and nutritional supplements suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, or a paste. These formulations may be prepared by methods known in the art, e.g., by means of conventional pan-coating, mixing, granulation or lyophilization processes.

Solid dosage forms for oral administration (capsules, tablets, pills, powders, granules and the like) may be prepared by mixing the active ingredient(s) with one or more acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the art. The tablets, and other solid dosage forms, may also be formulated so as to provide slow or controlled release of the active ingredient therein. They may be sterilized by, for example, filtration through a bacteria-retaining filter. These compositions may also optionally contain opacifying agents that release the active ingredient only, or preferentially, in a certain portion of the gastrointestinal tract, optionally, in a delayed manner. The active ingredient can also be in a microencapsulated form.

Liquid dosage forms for oral administration include acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

EXAMPLES

The following Examples describe various compositions of the present invention, which includes chlorogenic acid and at least one butyrate salt, and some in combination with at least one beta-hydroxybutyrate salt. In the following Examples, a subject will preferably receive, with each dose, 50 mg-500 mg chlorogenic acid; 50 mg-600 mg of short chain fatty acids (e.g., one or more of butyric acid, butyrate salts, propionic acid, propionate salts, acetic acid, or acetate salts); and, optionally, 50-10,000 mg of ketone (e.g., one or more beta-hydroxybutyrate salts). The invention provides that additional optimizing agents may be included in the compositions. For example, the compositions may further include potassium citrate, magnesium citrate, green tea extract, guarana extract, L-theanine, phenethylamine, L-tryptophan, valerian root extract, chamomile flower extract, passion fruit extract, ferulic acid, octacosanol, and/or one or more vitamins (such as Vitamin D).

Example 1 - Day Time Capsules

| Component | Amount/Capsule (mg) |
|---|---|
| Chlorogenic Acid | 375 |
| Butyrate Calcium Salt | 150 |
| Green Tea Extract | 100 |
| Guarana Extract | 50 |
| L-Theanine | 10 |
| Phenethylamine | 2 |
| Total per capsule(s) | 687 |

Example 2 - Nighttime Capsules

| Component | Amount/Capsule (mg) |
|---|---|
| Chlorogenic Acid | 225 |
| Butyrate Calcium Salt | 140 |
| L-Tryptophan | 600 |
| Valerian Root Extract | 5 |
| Chamomile Flower Extract | 5 |
| Passion Fruit Extract | 2 |
| Total per capsule(s) | 977 |

Example 3 - Day Time Capsules

| Component | Amount/Capsule (mg) |
|---|---|
| Chlorogenic Acid | 400 |
| Butyrate Calcium Salt | 100 |

Example 4 - Day Time Capsules

| Component | Amount/Capsule (mg) |
|---|---|
| Chlorogenic Acid | 400 |
| Butyrate Calcium Salt | 50 |

Example 5 - Day Time Capsules

| Component | Amount/Capsule (mg) |
|---|---|
| Chlorogenic Acid | 300 |
| Butyrate Calcium Salt | 180 |

Example 6 - Day Time Capsules, Powder, or Liquid

| Component | Amount (mg) |
|---|---|
| Chlorogenic Acid | 100-500 |
| Butyrate Calcium Salt | 50-250 |

Example 7 - Capsules (Serving Size = 3-4 Capsules)

| Component | Amount/Capsule (mg) |
|---|---|
| Chlorogenic Acid | 50 |
| Butyrate Sodium Salt; Butyrate Calcium Salt; and/or Butyrate Magnesium Salt | 500 |
| Beta Hydroxybutyrate Sodium Salt; Beta Hydroxybutyrate Calcium Salt; and/or Beta Hydroxybutyrate Magnesium Salt | 1,000 |
| Total per capsule(s) | 1,550 |

Example 8 - Capsules (Serving Size = 3-4 Capsules)

| Component | Amount/Capsule (mg) |
|---|---|
| Chlorogenic Acid | 100 |
| Butyrate Sodium Salt; Butyrate Calcium Salt; and/or Butyrate Magnesium Salt | 450 |
| Beta Hydroxybutyrate Sodium Salt; Beta Hydroxybutyrate Calcium Salt; and/or Beta Hydroxybutyrate Magnesium Salt | 1,000 |
| Total per capsule(s) | 1,550 |

Example 9 - Capsules (Serving Size = 3-4 Capsules)

| Component | Amount/Capsule (mg) |
|---|---|
| Chlorogenic Acid | 200 |
| Butyrate Sodium Salt; Butyrate Calcium Salt; and/or Butyrate Magnesium Salt | 350 |
| Beta Hydroxybutyrate Sodium Salt; Beta Hydroxybutyrate Calcium Salt; and/or Beta Hydroxybutyrate Magnesium Salt | 1,000 |
| Total per capsule(s) | 1,550 |

In each of the foregoing Examples 1-9, as mentioned above, the capsules may further include (1) one or more citrates (e.g., 5-100 mg of citrates), such as potassium citrate, magnesium citrate, and/or combinations thereof; (2) green tea extract (e.g., 5-100 mg of green tea extract); and/or (3) Vitamin D3 (cholecalciferol)(e.g., 10-200 international units (IU) of Vitamin D3). Other ingredients may include dicalcium phosphate and/or silicon dioxide. In each of the foregoing Examples 1-9, a subject having a body weight of about 150 pounds may consume one (1) to four (4) capsules per serving, while subjects having a body weight that exceeds 150 pounds may consume five (5) capsules per serving—along with, preferably, at least eight (8) ounces of water.

Example 10 - Dry Powder

| Component | Powder (mg) |
|---|---|
| Chlorogenic Acid | 500 |
| Butyrate Sodium Salt; Butyrate Calcium Salt; and/or Butyrate Magnesium Salt | 225 |

-continued

| Example 10 - Dry Powder | |
|---|---|
| Component | Powder (mg) |
| Optionally: | |
| Beta Hydroxybutyrate Sodium Salt; Beta Hydroxybutyrate Calcium Salt; and/or Beta Hydroxybutyrate Magnesium Salt | 3,500 |
| Total Per Serving | 4,225 |

In the foregoing Example 10, the ketogenic powder may further include (1) one or more citrates (e.g., 5-100 mg of citrates), such as potassium citrate, magnesium citrate, and/or combinations thereof; (2) green tea (e.g., 5-50 mg of green tea extract); and/or (3) Vitamin D3 (cholecalciferol) (e.g., 10-200 international units (IU) of Vitamin D3). Other ingredients may include ferulic acid and octacosanol. In addition, the compositions may further include natural and/or artificial flavors and sweeteners, dicalcium phosphate, and silicon dioxide. In the foregoing Example 10, a subject having a body weight of about 150 pounds may dissolve a single scoop of the powder in water or other preferred liquid until the power is adequately dissolved and then consume the fortified liquid.

Example 11—Concentrated Chlorogenic Acid

In this Example 11, the composition of the invention comprises, or consists essentially of, 100 mg-2,000 mg of chlorogenic acid, which is packaged in a form selected from the group consisting of an oral capsule, powdered form, and an aqueous or non-aqueous liquid. In such Example, the composition may, optionally, further include 100 mg-2,000 mg of butyrate salts.

Example 12—Effects on Brown Fat Cell Differentiation and Activation

In this Example 12, a composition of the present invention was administered to fibroblast cells that had been differentiated into brown adipocytes. More particularly, a test composition of the present invention was prepared that included a final concentration of 50 μM of chlorogenic acid and 2.4 mM of butyrate calcium salt. The differentiated brown adipocytes were incubated in 1,750 μL of the test composition of the present invention at room temperature for a 24-hour period. The differentiated brown adipocytes were viewed and analyzed via standard histology techniques pre- and post-treatment. As shown in the histology images of FIG. 1, after only a 24-hour period, the test composition of the present invention induced significant brown fat cell differentiation and activation.

Example 13—Effects on Human Weight Loss

In this Example 13, a composition of the present invention was administered to a group of six different human subjects over the course of seven weeks. The dietary habits of the subjects were not altered; however, each subject consumed two capsules by 9:30 am and two capsules at 1:00 pm each day. Each capsule included 225 mg of chlorogenic acid and 150 mg of butyrate calcium salt. The subjects also consumed at least 1 liter of water each day. As summarized in FIG. 2, each subject exhibited an impressive amount of weight loss, particularly given that the dietary habits of the subjects were not otherwise altered.

The many aspects and benefits of the invention are apparent from the detailed description, and thus, it is intended for the following claims to cover all such aspects and benefits of the invention that fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A composition consisting essentially of:

(a) chlorogenic acid;

(b) one or more butyrate salts selected from the group consisting of butyrate sodium salt, butyrate calcium salt, and butyrate magnesium salt, wherein the composition is packaged as an oral capsule or in powdered form, wherein the composition is effective to deliver via oral administration at least 50 mg of chlorogenic acid and at least 50 mg of the one or more butyrate salts to a person; and (c) one or more agents selected from the group consisting of potassium citrate, magnesium citrate, green tea extract, guarana extract, L-theanine, phenethylamine, L-tryptophan, valerian root extract, chamomile flower extract, passion fruit extract, ferulic acid, octacosanol, and one or more vitamins.

2. The composition of claim 1, wherein the composition includes:

(a) 100-500 mg of chlorogenic acid; and (b) 50-250 mg of butyrate calcium salt.

* * * * *